United States Patent [19]

Ling et al.

[11] Patent Number: 4,877,731
[45] Date of Patent: Oct. 31, 1989

[54] FERMENTATION PROCESS FOR CARBOXYLIC ACIDS

[75] Inventors: Lorraine B. Ling, Newark, Del.; Thomas K. Ng, Chadds Ford, Pa.

[73] Assignee: E. I. Du Pont De Nemours and Company, Wilmington, Del.

[21] Appl. No.: 212,300

[22] Filed: Jun. 27, 1988

[51] Int. Cl.$^4$ .......................... C12P 7/44; C12P 7/46; C12P 7/42; C12R 1/845
[52] U.S. Cl. .................................... 435/142; 435/145; 435/146; 435/939
[58] Field of Search ................ 435/142, 145, 146, 939

[56] References Cited

U.S. PATENT DOCUMENTS

| | | | |
|---|---|---|---|
| 2,326,986 | 8/1943 | Waksman | 435/145 |
| 2,327,191 | 8/1943 | Kane et al. | 435/145 |
| 2,861,922 | 11/1958 | Lubowitz et al. | 435/145 |
| 2,912,363 | 11/1959 | La Roe | 195/36 |
| 4,480,034 | 10/1984 | Hsieh | 435/142 |
| 4,564,594 | 1/1986 | Goldberg et al. | 435/139 |
| 4,608,338 | 8/1986 | Hsieh | 435/142 |

FOREIGN PATENT DOCUMENTS 0345368  3/1931 United Kingdom.
679087  9/1952 United Kingdom.
700316  11/1953 United Kingdom.

OTHER PUBLICATIONS

Rhodes et al., Appl. Microbiol., 7, 74–80 (1959).
Rhodes et al., Appl. Microbiol., 10, 9–15 (1962).
Derwent Abs 75-56395w/34 Orient Yeast J50048182.

Primary Examiner—Herbert J. Lilling

[57] ABSTRACT

An improved fermentation process for producing carboxylic acids is disclosed. The improvement comprises growing fungi of the genus Rhizopus in a culture medium containing a carbon source, a nitrogen source and inorganic salts, under conditions of controlled oxygen availability wherein the dissolved oxygen concentration for the cell growth phase is between 80% and 100% and where the dissolved oxygen concentration for the acid production phase is between 30% and 80%.

15 Claims, No Drawings

FERMENTATION PROCESS FOR CARBOXYLIC ACIDS

BACKGROUND OF THE INVENTION

1. Field of the Invention

This invention relates to a fermentation process for the production of certain carboxylic acids. More particularly, the invention concerns a method for improving the yield of certain carboxylic acids in Rhizopus cultures by limiting the amount of oxygen during the acid-production stage of the fermentation.

2. Background References

Production of certain carboxylic acids, e.g., fumaric acid, by fungi of the Rhizopus has been a subject of several patents and other contributions to the technical literature. Rhodes et al., *Appl. Microbiol.*, 7, 74–80 (1959), describe a series of fermentation experiments in which optimal conditions were sought for maximizing fumaric acid yields in *Rhizopus arrhizus* cultures. In a later publication, *Appl. Microbiol.*, 10, 9–15 (1962), Rhodes et al. describe preferred conditions for producing fumaric acid by fermentation of *Rhizopus arrhizus* in 20 liter fermenters. In particular, use of $CaCO_3$ to neutralize the resulting carboxylic acid as it is formed is disclosed.

Waksman, U.S. Pat. No. 2,326,986, describes a method for producing fumaric acid by fermentation of *Rhizopus nigricans*, or other fungi of the order Mucorales, in the presence of zinc and iron salts. Kane, et al., U.S. Pat. No. 2,327,191, disclose a process for producing fumaric acid by submerged aerobic fermentation of *Rhizopus nigricans*. Lubowitz, et al., U.S. Pat. No. 2,861,922, disclose use of nickel salts to promote fumaric acid production by Rhizopus fungi. La Roe, U.S. Pat. No. 2,912,363, describes improvements in fumaric acid yields by Rhizopus and related fungi which are attributable to limiting the concentration of nitrogen sources in culture media.

A number of patents and publications disclose that fats, fatty acids, or their derivatives can be added to microbial fermentation media as supplemental carbon sources, or as yield promoters in fermentation processes for producing glutamic acid and certain antibiotics. For example, U.K. Pat. Nos. 679,087 and 700,316 disclose the use of fats or fatty acids as carbon sources or supplements. Goldberg and Stieglitz, U.S. Pat. No. 4,563,594, disclose the use of fatty acid esters or triglycerides as culture medium additives to enhance the rate of production of carboxylic acids, especially fumaric acid.

Fermentation processes, especially those employing inexpensive and abundant carbon sources derived from biomass, offer alternative sources of supply of commercially important organic acids. Such organic acids include fumaric acid, which is utilized by the plastics industry in the manufacture of polyester and alkyd resins; lactic and malic acids, which are utilized by the food industry; and succinic acid, which is consumed in the manufacture of pharmaceuticals, plastics, and protective coatings. Thus, improved fermentation processes for producing these compounds are desirable.

SUMMARY OF THE INVENTION

The present invention provides an improvement in a fermentation process for producing carboxylic acids selected from the group consisting of fumaric acid, succinic acid, malic acid, and mixtures thereof, the improvement comprising growing fungi of genus Rhizopus in a culture medium with controlled dissolved oxygen levels in which the dissolved oxygen concentration is maintained between 80 and 100% for the cell-growth phase and 30–80% for the acid-production phase.

DETAILED DESCRIPTION OF THE INVENTION

The present invention provides an improved process for producing fumaric acid, succinic acid, malic acid or mixtures of these carboxylic acids by growth of fungi of the genus Rhizopus. The invention is characterized by a process improvement comprising limiting the dissolved oxygen levels and maintaining the dissolved oxygen concentration between 80 and 100% for the initial (i.e., cell-growth) phase and between 30 and 80% for the subsequent acid-production phase. Yields of these carboxylic acids, particularly fumaric acid, are enhanced when Rhizopus cultures are grown under conditions of controlled oxygen concentrations, especially when the concentration of oxygen is limited to less than about 80% during the acid-production phase. The increased yields of carboxylic acid production observed using the process of the invention are believed to be attributable to the regulation of the flow of glucose towards reaction with calcium carbonate rather than with oxygen under conditions of controlled oxygen availability.

Microorganisms

Suitable fungal species for the process of the invention are fungi of the genus Rhizopus. Examples of suitable species include *Rhizopus arrhizus, R. Oryzae,* and *R. nigricans*. Because of observed higher productivity, *R. arrhizus* is a preferred species. *R. Arrhizus* NRRL 1526, a strain described by Rhodes, et al., *Appl. Microbiol.*, 7 74–80 (1959), is a particularly preferred microorganism for the process of the present invention.

Culture Media

Various media formulations known to be suitable for Rhizopus fermentation can be employed in the process of the invention. Generally, a suitable medium will provide at least one carbon source, a nitrogen source and inorganic salts.

A suitable carbon source consists of an organic source of carbon such as glucose, sucrose, xylose, fructose, invert sugar, maltose, invert high test molasses, syrups, or various starches, grains, malted grains, cereal products or other materials containing any of the foregoing substances. Glucose is a preferred organic carbon source. When glucose is employed as an organic carbon source, it is preferred to use from about 10 to about 16 g glucose per 100 mL of medium.

During the acid-production stage of the fermentation, a suitable carbon source consists of an organic source of carbon such as defined above and an inorganic carbonate salt. A preferred inorganic carbonate salt is calcium carbonate.

Suitable nitrogen sources include such organic and inorganic sources as urea, ammonium chloride, ammonium sulfate, ammonium acetate, ammonium nitrate, ammonium biphosphate, asparagine and protein hydrolyzates, e.g. casein hydrolyzate and whey hydrolyzate. Of the foregoing, urea and ammonium sulfate are preferred.

To optimize yields of organic acids, particularly fumaric acid, available nitrogen in Rhizopus cultures should be limited to a range of about 10 to about 30 mmol available nitrogen per liter medium. Therefor, when ammonium sulfate is employed as a nitrogen source, it is preferred to employ from about 0.06 to about 0.18 g ammonium sulfate per 100 mL of medium.

The inorganic salts added to Rhizopus culture media should include sources of phosphate, sulfur, iron, magnesium, and zinc. Suitable sources of phosphate include monobasic or dibasic potassium phosphate, monobasic or dibasic sodium phosphate, ammonium biphosphate or mixtures thereof. Suitable inorganic salts employed in the fermentation include zinc sulfate, iron salts such as ferric tartrate or ferric chloride, and magnesium sulfate. Suitable sources of sulfur include ammonium sulfate, zinc sulfate and magnesium sulfate.

In a preferred fermentation medium, the carbon sources are glucose and calcium carbonate, the nitrogen source is ammonium sulfate, and potassium dihydrogen phosphate, magnesium sulfate, zinc sulfate, ferric chloride, and corn steep liquor or biotin are present.

In the preferred embodiment of this invention, the dissolved oxygen concentration is maintained between about 80% and 100% during the cell-growth phase of the fermentation. The preferred dissolved oxygen concentration during the acid-production phase is between about 30% and about 80%.

The cell-growth stage occurs during the initial phase of the fermentation, lasting from about 18 to about 28 h. The subsequent acid-production phase is allowed to proceed for a time sufficient to obtain optimum yields of the desired carboxylic acids. Times of about 3 to about 6 days are preferred. It should be appreciated that fermentation times are influenced to a significant degree by temperature, concentration and choice of microorganisms, nutrient concentration, and other factors known to those skilled in the art.

To realize the benefits of this invention, it is necessary to add calcium carbonate to the culture medium used during the acid-production stage of the fermentation. Calcium carbonate may also be added to the culture medium used during the cell-growth stage. The advantages of using calcium carbonate to neutralize the solution during fermentation are well-known in the art. However, it has not previously been recognized that the carbonate portion of $CaCO_3$ can also provide a source of carbon and oxygen atoms for the increased production of fumaric acid under conditions of limited oxygen availability. When oxygen levels are high during the acid-production phase, one molecule of glucose is converted to one molecule of fumarate, as shown in Equation 1. When oxygen levels are limited, one molecule of glucose is converted to two molecules of fumarate, as shown in Equation 2.

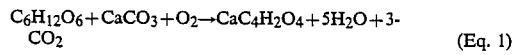

$$C_6H_{12}O_6 + CaCO_3 + O_2 \rightarrow CaC_4H_2O_4 + 5H_2O + 3\text{-}CO_2 \quad \text{(Eq. 1)}$$

$$C_6H_{12}O_6 + 2CaCO_3 \rightarrow 2CaC_4H_2O_4 + 4H_2O \quad \text{(Eq. 2)}$$

Process Conditions

Fermentation is conducted at a temperature of about 25° C. to about 35° C., preferably about 33° C. to about 35° C. A major product of the fermentation is usually fumaric acid, although succinic acid, malic acid, and other monocarboxylic and dicarboxylic acids can also be produced.

Production rates and yields in individual experiments can be significantly affected by such unpredictable factors as strain deterioration and adventitious impurities in media formulations and culture equipment. Accordingly, culture conditions should be continuously monitored and the productivity of fungal strains frequently checked.

After the process of this invention has gone to completion, the desired acid can be collected in pure form by conventional methods. Calcium salts of product acids can be converted to free carboxylic acids by acidification with mineral acid. Fungal mycelia and insoluble $CaSO_4$ can be removed by heating media to 80° C. to 100° C. for a brief period, followed by filtration. The resulting product acids can be recovered by crystallization.

The concentration of the microorganism required to practice the process of the invention efficiently is preferably about 0.1 to about 10 percent based on the volume of the reaction medium. Too little microorganism will cause a decrease in fermentation rate, and too large a quantity of microorganism will result in excess mycelium growth and decreased yields of acid relative to the amount of carbohydrate consumed.

The pH of the process medium is determined by the presence of excess calcium carbonate and is not maintained at a constant value during the fermentation. Generally, the pH of cultures grown in accordance with the process of the present invention should be maintained from about 4 to about 8, preferably from about 5 to about 7.

The following are illustrative examples of the invention in which all parts and percentages are by weight, and all degrees are Celsius unless otherwise noted.

GENERAL METHOD

Culture Maintenance

*Rhizopus arrhizus* NRRL 1526 was preserved by adding 1 mL of spore suspension to 16×150 mm test tubes, each containing 1 mL of 0.02M phosphate buffer, pH 7.0, in 0.1% Tween 80 and 205 glycerol. The tubes are stored frozen at −70° C.

Culture Media

The culture media used in the Examples were adapted from those previously described by Rhodes et al., *Appl. Microbiol.*, 7, 74–80 (1959), and are set forth in Table 1 below. All media were sterilized by autoclaving. Medium A, below, was used in Rhizopus spore development. Medium B was employed for Rhizopus vegetative seed fermentation, and Medium C was used for production or organic acids in aerobic fermentation experiments. The media were sterilized by autoclaving at 120° C. and 20 psig for 20 min. Calcium carbonate was sterilized dry inside the flasks for 24 h or as a 50% slurry in the fermenter for 1 h. The nitrogen source, ammonium sulfate or urea, was sterilized separately from other media components by autoclaving, and added aseptically to media mixtures prior to inoculation.

TABLE 1

| Ingredient (g/L) | Culture Media | | |
|---|---|---|---|
| | A Sporulation | B Germination | C Production |
| Glucose | 4.0 | 40.0 | 130 |
| Calcium Carbonate | 3.0 | 3.0 | 80 |
| Lactose | 6.0 | — | — |
| Glycerol | 10.0 (mL) | — | — |
| Urea | 0.6 | — | — |

TABLE 1-continued

| Ingredient (g/L) | Culture Media | | |
|---|---|---|---|
| | A Sporulation | B Germination | C Production |
| Ammonium Sulfate | — | 4.0 | 1.8 |
| $KH_2PO_4$ | 0.4 | 1.6 | 0.3 |
| $MgSO_4.7H_2O$ | 0.3 | 0.4 | 0.4 |
| $ZnSO_4.7H_2O$ | 0.088 | 0.044 | 0.044 |
| $FeCl_3.6H_2O$ | 0.0075 | 0.0075 | 0.0075 |
| Tartaric Acid | 0.0075 | 0.0075 | 0.0075 |
| Copper Sulfate | 0.005 | — | — |
| $MnSO_4.4H_2O$ | 0.05 | — | — |
| KCL | 0.4 | — | — |
| NaCl | 40.0 | — | — |
| Agar | 30.0 | — | — |
| Corn Steep Liquor (mL) | 1.0 (mL) | 0.5 (mL) | 0.5 |

Preparation of Inoculum

Working spore slants were prepared by adding 5 mL of sterile 0.05M sorbitan monooleate, to 1 mL of frozen spore solution and shaking well. One mL of the resulting spore suspension was plated on a Medium A agar slant which was incubated at 32° for 5-7 days.

Vegetative mycelial seed cultures were prepared by resuspending spores from 5-7 day medium A agar slants in 30 mL of 0.05M phosphate buffer, pH 6.8, containing 0.1% of polyoxyethylene sorbitan monooleate. The resulting spore suspensions were transferred to sterile Medium B, and incubated with agitation at 32° for 18-24 h. The resulting cell growth is referred to as "standard inoculum".

Fermentation

Fermentations were carried out in 3 L (2.5 L working volume) bioengineering glass fermenters (Model KLF 2000). All fermenters were equipped with automatic temperature controls, pH probes, $pO_2$ probes, sampling tubes, inoculation ports, and a control shaft with 2 disc turbine impellers (0.6 mm diameter).

Glucose (325 g) and 1-1.5 L of water were placed in the fermenter and sterilized at 121° C. for 20 min. Ammonium sulfate (4.5 g) and 50 mL of water were autoclaved at 121° C. for 20 min. $KH_2PO_4$ (0.75 g), $MgSO_4.7H_2O$ (1.0 g), $ZnSO_4.7H_2O$) (0.11 g), $FeCl_3.6H_2O$ (0.01875 g), tartaric acid (0.01876 g), corn steep liquor (1.25 mL) and 300 mL of water were autoclaved at 121° C. for 20 min. Calcium carbonate (200 g) was dry autoclaved for 24 h. After the glucose was sterilized and the temperature of the fermenter decreased to 60°-70° C., the calcium carbonate, ammonium sulfate and other salt solutions were transferred to the fermenter using sterile technique. Sterile distilled water was added to bring the final volume of the solution to 2.5 L.

Production of fumaric acid was initiated by the addition of 5% (v/v) of a standard inoculum of *Rhizopus arrhizus* NRRL 1526 to the fermenter. The temperature was maintained at 34° C. The aeration rate was 0.5 v/v and the dissolved oxygen concentration was controlled by the stirring rate which was maintained between 200 and 800 rpm.

Analysis

Fumarate, succinate, malate and α-ketoglutarate were analyzed as their methyl esters. Properly diluted samples (0.1 mL) were mixed with 0.05 mL of concentrated $H_2SO_4$ and 0.25 mL of methanol and incubated at 60° C. for 1 h in sealed autosampler vials. Water (0.25 mL) and chloroform (0.75 mL) were injected into the vials after cooling and the vials shaken to facilitate the extraction of methyl esters into the chloroform layer. For each sample, a 3 μL chloroform sample was then injected into a Hewlett-Packard 5880A gas chromatograph equipped with a Hewlett-Packard 7672A automatic liquid sampler. The following chromatographic conditions were used: 10% SP 2340 on chromosorb 100 w/a W column (1.8 m×0.32 cm); helium as carrier gas; injection port, 200° C.; f.i.d., 250° C.; oven, 2.5 min at 100° C. with a temperature increase of 20°/min to 180° for 8.0 min.

EXAMPLE 1

This example illustrates the effect of maintaining very low dissolved oxygen concentrations (less than 5%) during the acid-production stage of the fermentation:

| Time (hr) | Fumaric Acid (g/L) | Succinic Acid (g/L) | Malic Acid (g/L) | α-Keto-glutaric Acid (g/L) | Total Acid (g/L) |
|---|---|---|---|---|---|
| 0.0 | 0.1 | 0.0 | 0.0 | 0.0 | 0.1 |
| 21.5 | 6.4 | 0.0 | 10.6 | 2.2 | 19.2 |
| 26.5 | 9.6 | 0.0 | 16.7 | 2.9 | 29.2 |
| 30.0 | 14.4 | 2.1 | 12.5 | 3.1 | 32.1 |
| 45.5 | 30.0 | 3.1 | 11.6 | 4.9 | 49.6 |
| 51.5 | 34.7 | 3.2 | 11.6 | 5.0 | 54.5 |
| 53.0 | 36.6 | 3.3 | 11.6 | 4.9 | 56.4 |
| 68.5 | 43.9 | 3.6 | 10.6 | 6.0 | 64.1 |
| 74.0 | 38.5 | 3.4 | 9.8 | 6.2 | 57.9 |
| 143.0 | 49.7 | 4.4 | 10.2 | 8.9 | 73.2 |

EXAMPLE 2

This example illustrates the effects of maintaining a low dissolved oxygen concentration (approximately 10%) during the acid-production stage.

| Time (hr) | Fumaric Acid (g/L) | Succinic Acid (g/L) | Malic Acid (g/L) | α-Keto-glutaric Acid (g/L) | Total Acid (g/L) |
|---|---|---|---|---|---|
| 0.0 | 0.1 | 0.0 | 0.0 | 0.0 | 0.1 |
| 6.0 | 0.1 | 0.0 | 0.0 | 0.0 | 0.1 |
| 22.0 | 9.4 | 1.2 | 0.0 | 1.7 | 12.3 |
| 25.5 | 15.3 | 1.7 | 0.0 | 2.2 | 19.2 |
| 30.0 | 19.4 | 2.2 | 9.1 | 3.7 | 34.4 |
| 46.0 | 39.4 | 3.3 | 9.5 | 5.6 | 57.8 |
| 50.0 | 46.9 | 3.5 | 9.1 | 6.4 | 65.9 |
| 54.0 | 52.2 | 3.6 | 8.5 | 6.5 | 70.8 |
| 70.0 | 61.5 | 4.0 | 8.7 | 8.2 | 82.4 |
| 74.0 | 63.3 | 4.3 | 9.8 | 9.4 | 86.8 |
| 78.0 | 71.0 | 4.5 | 10.1 | 9.8 | 95.4 |
| 92.0 | 73.5 | 4.5 | 9.0 | 11.3 | 98.3 |
| 98.0 | 71.5 | 4.4 | 10.5 | 11.4 | 97.8 |
| 117.0 | 73.3 | 4.4 | 10.9 | 12.2 | 100.8 |
| 122.0 | 75.8 | 4.5 | 9.7 | 11.9 | 101.9 |
| 142.0 | 71.7 | 5.1 | 10.3 | 11.4 | 98.5 |

EXAMPLE 3

This example illustrates the effects of maintaining a moderate concentration of dissolved oxygen (approximately 40%) during the acid-production stage of the fermentation.

| Time (hr) | Fumaric Acid (g/L) | Succinic Acid (g/L) | Malic Acid (g/L) | α-Keto-glutaric Acid (g/L) | Total Acid (g/L) |
|---|---|---|---|---|---|
| 0.0 | 0.0 | 0.0 | 0.0 | 0.0 | 0.0 |
| 15.0 | 0.6 | 0.4 | 2.4 | 0.8 | 4.2 |
| 19.0 | 2.8 | 0.7 | 6.8 | 1.6 | 11.9 |
| 24.0 | 11.1 | 1.2 | 10.0 | 2.6 | 24.9 |
| 26.0 | 9.6 | 1.4 | 14.6 | 2.4 | 28.0 |
| 40.0 | 35.6 | 2.6 | 11.6 | 4.3 | 54.1 |
| 44.0 | 41.9 | 2.9 | 11.4 | 5.3 | 61.5 |
| 48.0 | 49.1 | 3.1 | 11.3 | 5.5 | 69.0 |
| 63.5 | 70.2 | 3.9 | 6.0 | 8.5 | 88.6 |
| 67.5 | 76.0 | 4.0 | 5.3 | 8.7 | 94.0 |
| 72.0 | 73.9 | 4.1 | 5.3 | 8.9 | 92.2 |
| 87.0 | 122.2 | 9.2 | 11.8 | 17.7 | 160.9 |
| 91.0 | 126.0 | 9.1 | 12.9 | 18.0 | 166.0 |

EXAMPLE 4

This example illustrates the effects of maintaining a moderate dissolved oxygen concentration (approximately 60%) during the acid-production phase of the fermentation.

| Time (hr) | Fumaric Acid (g/L) | Succinic Acid (g/L) | Malic Acid (g/L) | α-Keto-glutaric Acid (g/L) | Total Acid (g/L) |
|---|---|---|---|---|---|
| 0.0 | 0.6 | 0.4 | 0.0 | 0.0 | 1.0 |
| 6.0 | 0.3 | 0.2 | 0.0 | 0.0 | 0.5 |
| 21.5 | 12.3 | 1.4 | 17.1 | 0.0 | 30.8 |
| 25.5 | 8.3 | 1.7 | 25.8 | 0.0 | 35.8 |
| 29.5 | 21.7 | 2.1 | 25.7 | 6.8 | 56.3 |
| 45.5 | 70.0 | 3.7 | 20.8 | 14.8 | 109.3 |
| 53.5 | 93.1 | 4.1 | 11.9 | 16.7 | 125.8 |
| 70.0 | 109.1 | 4.2 | 12.1 | 17.4 | 142.8 |
| 74.0 | 108.7 | 4.3 | 12.8 | 17.7 | 143.5 |
| 97.0 | 103.2 | 4.2 | 12.5 | 17.7 | 137.6 |
| 118.0 | 121.0 | 4.5 | 13.3 | 18.8 | 157.6 |

EXAMPLE 5

This example illustrates the effects of maintaining a moderately high dissolved oxygen concentration (approximately 80%) during the acid-production phase of the fermentation.

| Time (hr) | Fumaric Acid (g/L) | Succinic Acid (g/L) | Malic Acid (g/L) | α-Keto-glutaric Acid (g/L) | Total Acid (g/L) |
|---|---|---|---|---|---|
| 0.0 | 0.6 | 0.1 | 0.0 | 0.0 | 0.7 |
| 6.0 | 0.2 | 0.2 | 0.0 | 0.0 | 0.4 |
| 22.0 | 13.5 | 1.5 | 17.6 | 0.0 | 32.6 |
| 26.0 | 16.0 | 2.0 | 24.0 | 6.1 | 48.1 |
| 30.0 | 27.7 | 2.5 | 26.1 | 7.2 | 63.5 |
| 46.0 | 69.7 | 4.1 | 26.1 | 13.9 | 113.8 |
| 51.5 | 105.2 | 4.8 | 22.8 | 15.4 | 148.2 |
| 70.0 | 125.4 | 5.1 | 13.2 | 17.7 | 161.4 |
| 76.5 | 135.3 | 5.3 | 14.2 | 18.3 | 173.1 |
| 142.0 | 130.0 | 4.8 | 15.6 | 19.0 | 169.4 |

EXAMPLE 6

This example illustrates the effects of maintaining high concentrations of dissolved oxygen (approximately 100%) during the acid-production phase of the fermentation.

| Time (hr) | Fumaric Acid (g/L) | Succinic Acid (g/L) | Malic Acid (g/L) | α-Keto-glutaric Acid (g/L) | Total Acid (g/L) |
|---|---|---|---|---|---|
| 0.0 | 0.2 | 0.2 | 0.0 | 0.0 | 0.4 |
| 15.0 | 0.1 | 0.5 | 2.4 | 0.0 | 3.0 |
| 19.0 | 0.4 | 1.1 | 5.7 | 0.0 | 7.2 |
| 24.0 | 9.0 | 1.2 | 10.5 | 2.1 | 22.8 |
| 26.0 | 12.0 | 1.3 | 10.7 | 2.5 | 26.5 |
| 40.0 | 30.9 | 2.6 | 14.2 | 4.2 | 51.9 |
| 44.0 | 41.2 | 3.0 | 13.3 | 5.2 | 62.7 |
| 48.0 | 45.9 | 3.1 | 12.1 | 5.5 | 66.6 |
| 63.5 | 64.6 | 3.9 | 6.9 | 8.5 | 83.9 |
| 67.5 | 68.2 | 3.9 | 6.5 | 8.4 | 87.0 |
| 72.0 | 72.6 | 4.2 | 7.2 | 9.2 | 93.2 |
| 87.0 | 73.5 | 4.5 | 7.3 | 9.5 | 94.8 |

The above results show that controlling oxygen concentration during the acid production phase increases the rate of formation of fumaric acid where the dissolved oxygen concentration is limited within a 30 to 80% of saturation range.

Although preferred embodiments of the invention have been illustrated and described hereinabove, it is to be understood that there is no intent to limit the invention to the precise constructions herein disclosed, and it is to be further understood that the right is reserved to all changes and modifications coming within the scope of the invention as defined in the appended claims.

What is claimed is:

1. In a fermentation process for producing carboxylic acids selected from the group consisting of fumaric acid, succinic acid, malic acid and mixtures thereof by growing fungi of the genus Rhizopus in a culture media comprising a carbon source, a nitrogen source and inorganic salts, wherein the process involves a cell-growth phase and an acid production phase, the improvement comprising growing said fungi under conditions of controlled dissolved oxygen availability in the culture medium, wherein the concentration of oxygen dissolved in the culture medium is maintained between about 80% and 100% of saturation for the cell-growth phase and between about 30% and 80% of saturation for the acid production phase.

2. A fermentation process for producing carboxylic acids selected from the group consisting of fumaric acid, succinic acid, malic acid and mixtures thereof comprising the following steps:
   a. growing fungi of the genus Rhizopus in a culture medium comprising a carbon source, a nitrogen source and inorganic salts, wherein the process involves a cell-growth phase and an acid production phase;
   b. maintaining within the culture medium a dissolved oxygen concentration of between about 80% and 100% of saturation for the cell-growth phase and between about 30% and 80% of saturation for the acid production phase.

3. A process according to claim 2 wherein the fungi used is selected from the group comprising *Rhizopus arrhizus, Rhizopus oryzae,* and *Rhizopus nigricans.*

4. A process according to claim 3 wherein the concentration of fungi is from about 0.1% to 10% of the culture medium by volume.

5. A process according to claim 4 wherein the carbon source at inoculation is glucose.

6. A process according to claim 5 wherein the nitrogen source is urea or ammonium sulfate.

7. A process according to claim 6 wherein the concentration of glucose at innoculation contains about 10 g to 16 g of glucose per 100 mL of culture medium.

8. A process according to claim 7 conducted in the presence of an excess of calcium carbonate.

9. A process according to claim 8 wherein the nitrogen source is ammonium sulfate and where there is from about 0.06 to 0.18 g ammonium sulfate per 100 mL of culture medium.

10. A process according to claim 9 conducted within a temperature range of about 33° C. to 35° C.

11. A process according to claim 10 wherein the culture medium includes inorganic salts containing phosphate, sulfur, iron, magnesium and zinc.

12. A process according to claim 11 wherein the inorganic salts included within the culture medium include potassium phosphate, zinc sulfate, magnesium sulfate, ferric tartrate and ferric chloride.

13. A process according to claim 12 wherein corn steep liquor is added to the growth medium.

14. A process according to claim 12 wherein biotin is added to the growth medium.

15. A process according to claim 13 or claim 14 wherein the fungi used is *Rhizopus arrhizus*.

* * * * *